United States Patent [19]
Haight et al.

[11] Patent Number: 6,124,474
[45] Date of Patent: Sep. 26, 2000

[54] SYNTHESIS OF CHIRAL 2-AZETIDINEMETHANOL COMPOUNDS

[75] Inventors: Anthony R. Haight, Wadsworth; John E. Lallaman, Zion; Gregory S. Wayne, Vernon Hills, all of Ill.

[73] Assignee: Abbott Laboratories, Abbott Park, Ill.

[21] Appl. No.: 09/468,503

[22] Filed: Dec. 21, 1999

[51] Int. Cl.[7] ...................... C07D 205/04; C07C 69/003; C07C 305/18
[52] U.S. Cl. ............................ 548/950; 548/953; 558/46; 560/102; 560/103; 568/648
[58] Field of Search ............................... 548/950; 558/46; 560/102, 103; 568/648

[56] References Cited

U.S. PATENT DOCUMENTS 5,472,958  12/1995  Gunn, Jr. et al. ........................ 514/210

OTHER PUBLICATIONS

Chong, J.M., et al., "Synthesis of N–Alkyl–3–Azetidinol Ethers", *Synthetic Comm.*, 25(4):603–611 (1995).

Duréault, A., et al. "Synthesis of Highly Functionalized Homochiral Azetidines and Azetidine–2–Carboxylic Esters", *Tetrahedron,* 49(20):4201–4210 (1993).

Wasserman, H.H., et al., "Preparation of β–Lactams from Azetidine–2–carboxylic Acids and Esters", *The Journ. of Organic Chemistry*, 46(15):2991–2999 (1961).

*Primary Examiner*—Fiona T. Powers
*Attorney, Agent, or Firm*—Michael J. Ward

[57] ABSTRACT

A process for preparing chiral isomers of N-protected 2-azetidinemethanol compounds, particularly N-(phenylmethyl)-2-azetidinemethanol and N-BOC-2-azetidinemethanol, and especially the (R)-isomers thereof, as well as O-substituted derivatives thereof.

12 Claims, No Drawings

SYNTHESIS OF CHIRAL 2-AZETIDINEMETHANOL COMPOUNDS

TECHNICAL FIELD

This invention relates to novel intermediates and a process for synthesis and isolation of chiral 2-azetidinemethanol compounds. Examples include such as N-(phenylmethyl)-2-azetidinemethanol and N-BOC-2-azetidinemethanol, and especially the (R)-isomer thereof, as well as O-substituted derivatives.

BACKGROUND OF THE INVENTION

Synthesis of an azetidine using a bisactivated diol system has previously been reported such as in the work of Durealt (*Tetrahedron*, 1993, 49, 4201). However the intermediates in this and similar work are oils. Incorporation of oils in a large scale synthesis is not desireable as purification can be tedious. This invention describes novel compounds and a method of synthesizing enantiomerically enriched 2-azetidinemethanol compounds that is amenable to scaleup due to the incorporation of unique protecting group strategies thus allowing for purification through crystalline intermediates of compounds leading to the azetidine derivatives.

SUMMARY OF THE INVENTION

This invention is directed at the synthesis of novel intermediates useful in a process for preparing chiral isomers of N-protected 2-azetidinemethanol compounds, particularly N-(phenylmethyl)-2-azetidinemethanol and N-BOC-2-azetidinemethanol, and especially the (R)-isomers thereof, as well as O-substituted derivatives thereof. These compounds are useful as intermediates in the synthesis of cholinergic channel modulators. Cholinergic channel modulators may be useful as central nervous system acting agents such as analgesics and neuroprotectives.

This invention relates to novel intermediates 3 and 4 as shown in Scheme I. Intermediate 3 is a diol compound of the formula,

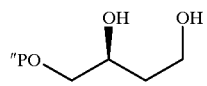

(3)

wherein P" is a hydroxy protecting group.
Intermediate 4 is a compound of the formula

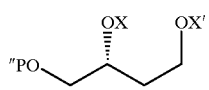

(4)

wherein P" is as described above and X and X' are independently —SO₂R', wherein R' is selected from the group consisting of alkyl, haloalkyl, aryl, and arylakyl.

This invention also relates to a process of Scheme I for preparing novel (R)-N-protected-2-azetidinemethanol compounds of formula (6),

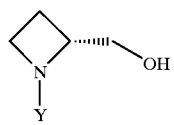

6 wherein Y is a nitrogen protecting group; said process comprising treating S-1,2,4-butanetriol with an aldehyde or acetal and an acid catalyst in solvent to give a alcohol substituted cyclic dioxane compound (1); treating the primary hydroxyl group of the dioxane compound (1) with a hydroxy-protecting reagent to give a protected dioxane compound (2); hydrolytically treating the protected dioxane compound (2) to provide a diol compound (3); and treating the diol compound (3) with an activating agent to give a di-activated compound (4).

Compound (4) may be further treated with a primary amine at an elevated temperature to displace the activated groups and closing the ring to give the N-protected, hydroxy-protected compound of formula (5), wherein P" is a hydroxy-protected group and Y is a nitrogen protecting group. Preferable nitrogen protecting groups for compound (5) include, but are not limited to, alkyl, aryl and arylalkyl.

Once the N-protected, hydroxy-protected compound (5) is obtained, the nitrogen atom may optionally be deprotected and re-protected, then deprotecting the hydroxyl moiety, and isolating the desired chiral compound (6). The re-protection of the nitrogen atom is preferably done using a 1,1-dimethylethoxycarbonyl group.

The solvent used with the acid catalyst to provide the substituted cyclic dioxane compound (1) is selected from, but not limited to, toluene and dichloromethane. The preferred acid catalyst is sulfonic acid.

P" is a hydroxy protecting group selected from the group consisting of esters, ethers, silyl ethers, carbamates, and carbonates. P" is preferably selected from the group consisting of benzoate and p-phenylbenzoate.

X and X' are independently —SO₂R' wherein R' is selected from the group consisting of alkyl, haloalkyl, and aryl. Preferable X and X' groups are sulfonate leaving groups and a preferable R' is selected from the group consisting of 4-methylphenyl, 4-methoxyphenyl, methyl, or trifluoromethyl.

Scheme 1

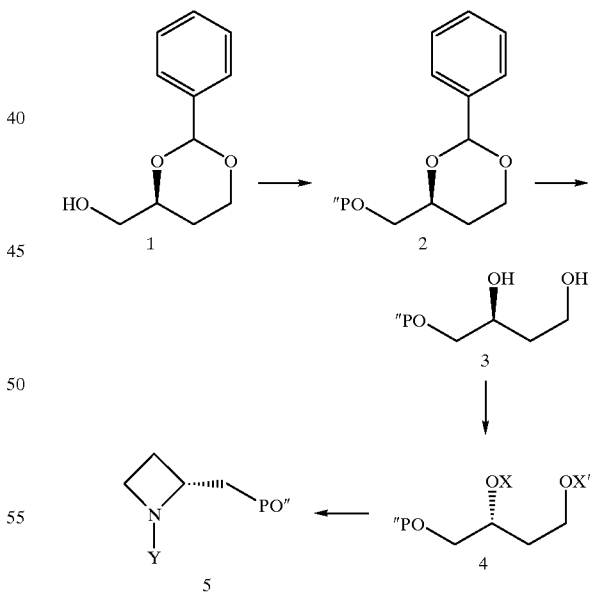

All citations herein are incorporated by reference.

All substituents in this disclosure are named so that the linker to the parent molecular moiety is the last substitutent in the name. For example, alkylcarbonyl refers to an alkyl substitent appended to the aryl compound through a carbonyl moiety.

The following definitions are used in this application. BOC, Boc, or t-Boc are abbreviations for 1,1- dimethylethoxycarbonyl, CBZ is an abbreviation for phenylmethoxycarbonyl (i.e., benzyloxycarbonyl).

Substituted benzyl refers to a phenylmethyl compound where an additional alkyl or aryl group may be attached to the methyl group or where an alkyl, aryl, alkoxy, aryloxy, or halogen may be attached to the phenyl group.

The term "alkyl," as used herein, refers to a straight or branched chain hydrocarbon containing from 1 to 10 carbon atoms. Representative examples of alkyl include, but are not limited to, methyl ethyl, n-propyl, n-butyl, sec-butyl, iso-butyl, tert-butyl, n-pentyl, isopentyl, neopentyl, n-hexyl, 3-methylhexyl, 1-ethylpropyl, 2,2-dimethylpentyl, 2,3-dimethylpentyl, n-heptyl, n-octyl, n-nonyl, n-decyl, and the like.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, and the like.

The term "aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 substituents independently selected from alkenyl, alkoxy, alkoxycarbonyl, alkoxycarbonylalkyl, alkyl, alkylcarbonyl, alkylcarbonyloxy, alkylcarbonyloxyalkyl, alkylsulfinyl, alkylsulfonyl, alkynyl, amido, amidoalkyl, arylalkoxycarbonyl, arylalkoxycarbonylalkyl, arylcarbonyloxy, arylcarbonyloxyalkyl, aryloxycarbonyl, aryloxycarbonylalkyl, arylsulfonyl, cyano, halo, haloalkyl, haloalkoxy, nitro, sulfamyl, sulfamylalkyl.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 1,1-dimethyl-2-phenylethyl, 3-phenylpropyl, 2-naphth-2-ylethyl, and the like.

The term "aryloxy," as used herein, refers to an aryl group, as defined herein, appended to the parent molecular moiety through an oxy moiety, as defined herein. Representative examples of aryloxy include, but are not limited to, phenoxy, naphthyloxy, 3-bromophenoxy, 4-chlorophenoxy, 4-methylphenoxy, 3,5-dimethoxyphenoxy, and the like.

The term "haloalkyl," as used herein, refers to at least one halogen, as defined herein, appended to the parent molecular moiety through an alkyl group, as defined herein. Representative examples of haloalkyl include, but are not limited to, chloromethyl, trichloromethyl, 1,1-dichloroethyl, 2-fluoroethyl, trifluoromethyl, 2,2,2-trifluoroethyl, 2,2,2-trifluoro-1-(trifluoromethyl)-1-(methyl)ethyl, pentafluoroethyl, 2-chloro-3-fluoropentyl, and the like.

The term "hydroxy-protecting group" or "O-protecting group" refers to a substituent which protects the hydroxyl groups against undesirable reactions during the synthetic procedures in this synthesis. Examples of hydroxy-protecting groups include, but are not limited to, substituted and unsubstituted benzyl and benzyl ethers, for example, benzyl, p-methoxybenzyl, p-phenylbenzyl, p-methylbenzyl and the like, substituted ethyl ethers, for example, 2,2,2-trichloroethyl and t-butyl; silyl ethers, for example, trimethylsilyl, t-butyldimethylsilyl and t-butyldiphenylsilyl, carbonates, for example, methyl, ethyl, tert-butyl and the like; and carbamates, for example, N,N-dimethyl, N-phenyl, N-benzyl, and the like. Commonly used hydroxy-protecting groups are disclosed in T. H. Greene and P. G. M. Wuts, *Protective Groups in Organic Synthesis*, 2nd edition, John Wiley & Sons, New York (1991). The precise conditions of removal of the protecting groups depend on the nature of the protecting group, and these are well described in suitable reference sources, such as Greene and Wuts (op. cit.).

The term "hydroxy-protecting reagent" refers to a "hydroxy-protecting group" as defined above in a suitable medium such as solvent which allows a reaction to proceed such that protection of the hydroxy moiety occurs.

The term "nitrogen protecting group" refers to a group placed on a nitrogen atom for purposes or protecting an intermediate from an undesired reaction of the amnine with a reagent. Nitrogen protecting groups include moieties such as Boc, Cbz, aryl substituted Cbz, trifluoroacetyl, benzenesulfonyl, aryl substituted benzensulfonyl, benzyl, substituted benzyl, and others commonly known in the art (see T. W. Greene and P. G. M. Wuts, *Protective Groups in Organic Synthesis*, 2nd edition, John Wiley & Sons, New York (1991). The precise conditions of N-deprotection depend on the nature of the protecting group, and these are well described in suitable reference sources, such as Greene and Wuts (op. cit.) or computer databases such as the Synopsys Protecting Groups Database (Synopsys Scientific Systems, LTD., Leeds, UK).

The starting material is S-1,2,4-butanetriol which is readily available from reduction of L-malic acid. Selective protection of the 1-hydroxyl group of (1) is achieved by a two-step method, with the first step being the protection of the 2,4-diol as the cyclic acetal (2), by reaction with benzaldehyde or an acetal of benzaldehyde and an acid catalyst in a suitable solvent, such as toluene, benzene, methylene chloride or the like, which may result in as much as a 6:1 selectivity of the protected 2,4-diol over the protected 1,2-diol.

For the second step of protecting the primary hydroxyl group of (1), a suitable acid stable protecting group is required to give compound (2). Protecting groups such as the phenylmethyl ether, benzoate, or p-phenylbenzoate, for example, may be employed. Other protecting groups known to the art may be employed as well (see Greene and Wuts, op. cit.). A protecting group which provides for a solid product is preferred for ease of isolation and purification during the process. One preferred protecting group is para-phenylbenzoate, because the product is a white solid which is easily purified by recrystallization. Deprotection of the acetal (2) by acid hydrolysis provides the 2,4-diol (3). Treatment of (3) with a suitable activating agent, such as methanesulfonyl chloride, p-toluenesulfonyl chloride, p-methoxyphenylsulfonyl chloride, thionyl chloride, or the like, gives the di-activated compound (4). A preferred activating agent is methanesulfonyl chloride. This reaction is performed in an inert solvent such as, but not limited to, THF, dimethylformamide, dichloromethane, or the like, in the presence of a base such as triethylamine or pyridine or the like; or alternatively, the reaction may be achieved in neat pyridine.

Compound (4) is next converted into the protected azetidine compound (5) by displacement of both activating groups with a primary amine, preferably phenylmethylamine. The reaction is performed in an inert solvent such as methylene chloride, or preferably acetonitrile, in the presence of a base, such as triethylamine, diisopropylamine or the like, for example, at a temperature of from about 60° C. to about 75° C. for a period of about 12 hours to about 24 hours.

The azetidine (5) may then be treated with hydrogen over palladium carbon catalyst to remove the benzyl protecting group, and this newly deprotected intermediate is treated with di-t-butyldicarbonate in-situ to give the N-Boc protected compound. Subsequent hydrolytic deprotection of the N-Boc protected compound gives the N-Boc-azetidinemethanol compound, which is useful as an intermediate in the synthesis of cholinergic channel modulators.

The compounds and processes of the present invention will be better understood in connection with the following examples, which are intended as an illustration of and not a limitation upon the scope of the invention.

EXAMPLE I

Step 1a. 2S, 4S-4-hydroxymethyl-2-phenyl-1,3-dioxane

A mixture of S-1,2,4-butanetriol (20 g; 189 mmol), benzaldehyde (22.1 g, 208 mmol) and p-toluenesulfonic acid (380 mg; 2 mmol) in toluene (1000 mL) was heated at reflux, using a Dean-Stark trap. After 7 hours, the reaction was allowed to cool to room temperature and stirred for 12 hours. Aqueous 40% NaHSO$_3$ (2000 mL) was added, and the mixture was stirred at room temperature for 1 hour. The organic layer was separated and washed with saturated aqueous sodium bicarbonate. Concentration under vacuum provided the title compound (25.85 g, 71% yield) as a yellow/brown oil.

Step 1b. 2S, 4S-4-(1,1'-diphenyl-4-carboxy)hydroxymethyl-2-phenyl-1,3-dioxane

The compound from Step 1a (25.7 g; 132 mmol) was dissolved in CH$_2$Cl$_2$ (500 mL), along with triethylamine (26.8 g; 265 mmol). The reaction mixture was cooled in an ice bath, then 4-biphenylcarbonyl chloride (30.1 g; 139 mmol) was added in one portion.

The reaction was allowed to warm to room temperature, then stirred for 1 hour. The reaction mixture was washed with water and concentrated under vacuum to leave a brown liquid residue. Methylene chloride was chased from this material with methanol, and this residue was crystallized from methanol, filtered and dried to provide the title compound (29.85 g, 60% yield) as a tan crystalline solid. NMR (CDCl$_3$) Proton: 1.61–1.68 (m, 1H), 1.96–2.08 (m, 1H), 3.99–4.08 (m, 1H), 4.28–4.38 (m, 2H), 4.47 (d, 2H, J=5Hz), 5.59 (s,1H), 7.33–7.54 (m, 8H), 7.61–7.69 (m, 4H), 8.14 (m, 2H). Carbon: 27.67, 66.62, 66.92, 74.90, 101.21, 126.07, 127.04, 127.25, 128.15,128.23, 128.64, 128.86, 128.90, 130.22, 138.26, 139.93, 145.80, 166.30.

Step 1c. 2S-1,2,4-butanetriol-1-(1,1'-diphenyl-4-carboxylate).

The compound from Step 1b (70 g; 187 mmol) was suspended in acetic acid (900 mL) and H$_2$O (200 mL) and heated to 40° C. After 3 hours, the acetic acid was removed under vacuum, and the residue was chased with toluene. The resultant solid was recrystallized from toluene, filtered, washed with toluene, and dried in a vacuum oven to provide the title compound (38.7 g, 72% yield) as a white crystalline solid. NMR (DMSO) Proton: 1.43–1.54 (m, 2H), 3.41 (q, 2H, J=6Hz), 3.74–3.86 (m, 1H), 3.99–4.10 (m, 2H), 4.35 (t, 1H, J=5Hz), 4.85 (d, 1H, J=5Hz), 7.26–7.36 (m, 3H), 7.57 (m, 2H), 7.66 (m, 2H), 7.92 (m, 2H). Carbon: 36.65, 57.58, 55.55, 69.06, 126.93, 127.04, 128.45, 128.75, 129.14, 130.02, 138.93, 144.72, 165.66. MS m/z 287 (M+H)$^+$.

Step 1d. 2S-2,4-dimethanesulfonyl-1,2,4-butaneriol-1-(1,1'-diphenyl-4-carboxylate)

The diol compound from Step 1c (35 g, 122 mmol) was dissolved in in CH$_2$Cl$_2$ (500 mL) and triethylamine (37.1 g; mmol). With ice-bath cooling, methanesulfonyl chloride (42.0 g; 367 mmol) was added dropwise. The reaction was then warmed to room temperature and stirred for 1 hour. The reaction mixture was diluted with CH$_2$Cl$_2$, and the mixture was washed with water. After drying over MgSO$_4$, the extract was concentrated under vacuum, then chased with methanol. Recrystallization from- methanol provided the title compound as a white crystalline solid (43.1 g, 80% yield). NMR (CDCl$_3$) Proton: 2.22–2.29 (m, 2H), 3.09 (s, 3H), 3.11 (s, 3H), 4.39–4.52 (m, 3H), 4.61–4.66 (m, lH), 5.24 (m, 1H), 7.41–7.51 (m, 3H), 7.61–7.71 (m, 3H), 8.14 (m, 2H). Carbon: 31.31, 37.48, 38.79, 64.84, 65.21, 75.63, 127.26, 127.80, 128.31, 128.96, 130.27, 139.72, 146.31, 165.80.

Step 1e 2S-N-benzyl-2-azetidinylmethoxy (1,1'-diphenyl-4-carboxylate)

The dimesylate compound from Step 1d (5 g, 11 mmol) was dissolved in acetonitrile with triethylamine (5.7 g; 56 mmol) and benzyl amine (1.2 g). The reaction was heated at reflux for 17 hours. The reaction mixture was concentrated and chased with toluene. The residue was dissolved in CH$_2$Cl$_2$ (125 mL), washed with brine (3×50 mL) and concentrated to give the title compound as a yellow/brown oil (4.0 g, 99% yield). NMR CDCl$_3$ Proton: 2.06–2.14 (m, 2H), 2.92–2.98 (m, 1H), 338 (m, 1H), 3.57–3.65 (m, 1H), 3.59 (d, 1H, J=13Hz), 3.88 (d, 1H, J=13Hz), 4.22–4.38 (m, 2H), 7.35–7.48 (m, 3H), 7.60–7.70 (m, 4H), 8.07 (d, 2H, J=9Hz).

Step 1f. 2S-N-t-butyloxycarbonyl-2-azetidinylmethoxy (1,1'-diphenyl-4-carboxylate)

The compound from Step 1e (1.2 g; 3.4 mmol) was dissolved in wet THF (30 mL), along with di-t-butyl dicarbonate (1.5 g). Pd(OH)/C (120 mg, 20%) was added, and the vessel was charged with 40 psi H$_2$. After 24 hours at 50° C., HPLC analysis showed the reaction to be complete. After the catalyst was removed by filtration, and N,N-dimethylethylenediamine (2 g) was added to the filtrate. After stirring for 1 hour, the THF was removed and replaced with ethyl acetate. This solution was then washed with 15% citric acid, sodium bicarbonate solution, dried over MgSO$_4$, the and concentrated to an oil. NMR (CDCl$_3$) Proton÷1.44 (s, 9H), 2.15–2.25 (m, 1H), 2.32–2.44 (m, 1H), 3.86–3.96 (m, 2H), 4.47 (dd, 1H, J=4,11 Hz), 4.50–4.58 (m, 1H), 4.66 (dd, 1H, J=4, 11 Hz), 7.38–7.50 (m,3H), 7.61–7.69 (m, 4H), 8.14 (d, 2H, J=9Hz).

Step 1g. 2S-N-t-butyloxycarbonyl-2-azetidinylmethanol

The compound from Step If (I g; 2.72 mmol) was dissolved in THF (25 mL) and methanol (25 mL). To this was added a solution of LiOH (280 mg in 5 mL water). The reaction was stirred for 2 hours, then concentrated to a slurry. The slurry was filtered, and the filter cake was washed with water. The aqueous filtrate was extracted with ethyl acetate. The combined organics were concentrated to an oil, which was taken up in ethyl acetate and filtered to remove residual solids, then concentrated to give the title compound as a colorless oil (530 mg; 104%). The analytical data was in agreement with that of the known reference compound. NMR (CDCl$_3$) Proton: 1.45 (s, 9H), 1.82–2.02 (m, 1H), 2.12–2.25 (m, 1H), 3.74–3.92 (m, 4H), 4.38–4.52 (m, 1H).

What is claimed is:

1. A compound of the formula

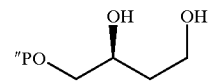

wherein P" is selected from the group consisting of phenylmethyl ether, benzoate, and para-phenylbenzoate.

2. A compound of claim 1 wherein P" is para-phenylbenzoate.

3. A compound of the formula

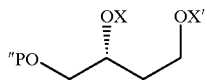

wherein P" is selected from the group consisting of phenylmethyl ether, benzoate, and p-phenylbenzoate, and X and X' are independently —SO$_2$R' wherein R' is selected from the group consisting of alkyl, haloalkyl, aryl, and arylalkyl.

4. A compound of claim 3 wherein R' is methyl.

5. A compound of claim 3 wherein P" is para-phenylbenzoate.

6. A process of preparing a (R)-N-protected-2-azetidinemethanol compound of the formula

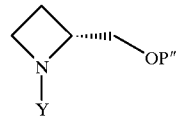

wherein P" is a hydroxy protecting group and Y is a nitrogen protecting group, comprising:

(a) treating S-1,2,4-butanetriol with an aldehyde or acetal and an acid catalyst in solvent to give a alcohol substituted cyclic dioxane compound;

(b) treating the primary hydroxyl group of the dioxane compound with a hydroxy-protecting reagent to give a protected dioxane compound;

(c) hydrolytically treating the protected dioxane compound to provide a diol compound;

(d) treating the diol compound with an activating agent to give a di-activated compound; and (e) treating the di-activated compound with a primary amine to give a N-protected, hydroxy-protected compound.

7. A process of claim 6 wherein said Y is selected from alkyl, aryl and arylalkyl.

8. A process of claim 7 wherein Y is aryalkyl.

9. A process of claim 8 wherein Y is benzyl.

10. A process of claim 6 wherein the activating agent is methanesulfonyl.

11. A process of claim 6 wherein in step (b), the hydroxy protecting group is selected from the group consisting of phenylmethyl ether, benzoate, and p-phenylbenzoate.

12. A process of claim 6 wherein P" is para-phenylbenzoate.

* * * * *